(12) United States Patent
Sun et al.

(10) Patent No.: US 6,734,435 B2
(45) Date of Patent: *May 11, 2004

(54) PHOTO-IONIZATION DETECTOR AND METHOD FOR CONTINUOUS OPERATION AND REAL-TIME SELF-CLEANING

(75) Inventors: Hong T. Sun, Los Gatos, CA (US); Peter C. Hsi, Fremont, CA (US)

(73) Assignee: RAE Systems, Inc., Sunnyvale, CA (US)

(*) Notice: Subject to any disclaimer, the term of this patent is extended or adjusted under 35 U.S.C. 154(b) by 375 days.

This patent is subject to a terminal disclaimer.

(21) Appl. No.: 09/870,179

(22) Filed: May 29, 2001

(65) Prior Publication Data

US 2002/0179846 A1 Dec. 5, 2002

(51) Int. Cl.[7] .................. H01J 47/02; G01N 27/64; G01N 27/66
(52) U.S. Cl. .................. 250/423 P; 250/287; 250/288; 250/389; 250/374; 250/281
(58) Field of Search .................. 250/281, 282, 250/288, 389, 374, 423 P; 430/5; 422/186.15; 73/865.8

(56) References Cited

U.S. PATENT DOCUMENTS

| | | |
|---|---|---|
| 3,933,432 A | 1/1976 | Driscoll |
| 4,013,913 A | 3/1977 | Driscoll et al. ............. 313/242 |
| 4,376,893 A | 3/1983 | Whetten ..................... 250/374 |
| 4,398,152 A | 8/1983 | Leveson ..................... 324/465 |
| 4,429,228 A | 1/1984 | Anderson .................. 250/374 |
| 4,454,425 A | 6/1984 | Young |
| 4,704,536 A | 11/1987 | Sugiyama et al. .......... 250/381 |
| 4,778,998 A | 10/1988 | Carnahan .................... 250/382 |
| 4,804,846 A | 2/1989 | Hall ............................ 250/379 |
| 5,028,544 A | 7/1991 | Rasulev et al. ............. 436/161 |
| 5,393,979 A | 2/1995 | Hsi ............................. 250/382 |
| 5,431,714 A | 7/1995 | Burtscher et al. ............... 95/57 |
| 5,504,328 A | 4/1996 | Bonser ........................ 250/288 |
| 5,520,060 A | 5/1996 | Gysi et al. ................... 73/865.8 |
| 5,540,898 A | 7/1996 | Davidson ............... 422/186.15 |
| 5,561,344 A | 10/1996 | Hsi ............................. 313/494 |
| 5,572,137 A | 11/1996 | Jones ......................... 324/464 |
| 5,604,059 A | 2/1997 | Imura et al. .................... 430/5 |
| 5,728,586 A | 3/1998 | Platzer ....................... 436/153 |

(List continued on next page.)

FOREIGN PATENT DOCUMENTS

| | | | |
|---|---|---|---|
| DE | 4320607 | 12/1994 | .......... G01N/27/64 |
| DE | 19750788 | 6/1999 | .......... H01J/47/02 |
| EP | 0524022 | 1/1993 | .......... G01N/27/66 |
| EP | 0694783 | 1/1996 | .......... G01N/27/66 |
| EP | 0995989 A1 | 4/2000 | |
| EP | 1243921 A2 | 9/2002 | |
| GB | 1042359 | 9/1966 | .......... H01J/37/32 |

OTHER PUBLICATIONS

Patent Abstract of Japan Publication No. 60066155 (Shimazu Seisakusho KK), Apr. 16, 1985.

*Primary Examiner*—John R. Lee
*Assistant Examiner*—David A Vanore
(74) *Attorney, Agent, or Firm*—David T. Millers

(57) ABSTRACT

A photo-ionization detector (PID) including two detection units controls gas flows through the ionization chambers of the detection units for real-time self-cleaning and measurement. Operation of the PID can include flowing gas through the ionization chamber of one detection unit to measure the volatile gas concentration while stopping gas flow through the ionization chamber of the other detection unit. A UV lamp converts oxygen contained in the closed ionization chamber to ozone, which removes contamination in the closed ionization chamber, Continuous gas flows can alternate between one ionization chamber to the other. Alternatively, a PID with only one gas detection unit intermittently interrupts the flow of the ambient gas in the ionization chamber.

34 Claims, 4 Drawing Sheets

U.S. PATENT DOCUMENTS

| | | |
|---|---|---|
| 5,733,833 A | 3/1998 | Abe et al. .................... 501/137 |
| 5,773,833 A | 6/1998 | Hsi ............................ 250/382 |
| 5,855,850 A | 1/1999 | Sittler ........................ 422/98 |
| 5,968,837 A | 10/1999 | Döring et al. .............. 436/173 |
| 6,225,633 B1 * | 5/2001 | Sun et al. ................... 250/389 |
| 6,313,638 B1 | 11/2001 | Sun et al. |
| 6,320,388 B1 | 11/2001 | Sun et al. |
| 6,333,632 B1 | 12/2001 | Yang et al. |
| 6,469,303 B1 | 10/2002 | Yang et al. |
| 6,509,562 B1 | 1/2003 | Sun et al. |

* cited by examiner

PHOTO-IONIZATION DETECTOR AND METHOD FOR CONTINUOUS OPERATION AND REAL-TIME SELF-CLEANING

BACKGROUND OF THE INVENTION

This invention relates to a volatile gas detector, particularly to a continuously operated photo-ionization detector (PID), and a method for real-time self-cleaning of the volatile gas detector.

Photo-ionization detectors (PIDs) can detect volatile gases. FIG. 1 shows a conventional portable PID 10 that includes an ultraviolet (UV) lamp 12 and an ionization chamber 14. UV lamp 12 produces UV light including UV photons having energy up to 8.4 electron volts (eV) or more. The UV photons pass through an optical window 16 into ionization chamber 14. In ionization chamber 14, the UV photons collide with and ionize volatile gas molecules having ionization potentials below the energy of the photons, creating ions and electrons.

PID 10 further includes an ion detector 18 having a pair of electrodes 20 and 22, which are typically made of a metal. Ion detector 18 has a high voltage (150 V or more) applied across electrodes 20 and 22 to generate an electrical field. In particular, electrode 22 is biased to a high voltage to attract negatively charged particles (electrons) and repel positively charged particles (ions), and electrode 20 is grounded to collect the positively charged particles (ions). The movement of the ions to electrode 22 produces a current, from which the concentration of the volatile gas can be determined.

After an extended use of PID 10, contamination, such as a coating of metal atoms, oil film, dust particles, and/or other polymer-like coating, often builds up inside ionization chamber 14, especially on electrodes 20 and 22 and window 16. The contamination on electrodes 20 and 22 reduces the accuracy of volatile gas concentration measurement by preventing the ion and electron collection of electrodes 20 and 22. The contamination on window 16 decreases the intensity of the UV light introduced to ionization chamber 14 from UV lamp 12, and thus reduces the accuracy of volatile gas concentration measurement. Accordingly, PID 10 must be regularly dissembled and cleaned to remove such contamination. A traditional PID usually loses sensitivity to gas by 10% to 20% per day because of contamination during continuous operation.

U.S. Pat. No. 6,225,633, to Sun et al., entitled "Photo-ionization Detector For Volatile Gas Measurement and Method for Self-Cleaning The Same", issued on May 1, 2001 and assigned to the assignee of the present invention, which is herein incorporated by reference in its entirety, describes a PID that is capable of self-cleaning. After an extended use, the PID is stopped from measuring the volatile gas concentration, and the contamination in the PID is removed without dissembling the PID. When removing the contamination inside the ionization chamber of the PID, the gas sample, which may include the volatile gas molecules, is prevented from flowing through the ionization chamber and thus is trapped within the ionization chamber. Then, the UV light from the UV lamp converts oxygen in the gas sample to ozone, which is a strong oxidant. The ozone etches and removes the contamination inside the ionization chamber, that is, the contamination on electrodes and window. After the contamination has been etched and removed, the products of the contamination removal are discharged from the ionization chamber. After self-cleaning for a period of time, the PID can almost fully recover the sensitivity that was lost due to contamination. But this technique does not offer a continuous operation which is required in most fixed systems for processing control and safety protection.

Although being capable of self-cleaning, the PID of U.S. Pat. No. 6,225,633 has several shortcomings. First, when the gas sample includes little or no oxygen, the effectiveness of the self-cleaning will be decreased. Second, while the PID is being self-cleaned, the PID cannot measure the concentration of volatile gas molecules existing in the ambient area. In other words, the PID cannot perform real-time measurement of the concentration of volatile gas molecules.

SUMMARY

During the normal operation of PIDs, the effectiveness of PIDs diminishes due to the build-up of contamination, such as a coating of metal atoms, oil film, dust particles, or other polymer-like coating substances, in an ionization chamber of the PID. The contamination on an optical window of the PID can gradually decrease the UV intensity from a UV lamp to the ionization chamber, resulting in inaccurate measurement of volatile gas concentration. Accordingly, a user must dissemble the PID to clean ionization chamber. Further, while the PID is being cleaned, the volatile gas concentration cannot be measured.

The present invention provides PIDs capable of self-cleaning and real-time measurement of the concentration of volatile gas molecules existing in the environment. The invention also provides methods that enable the PIDs to continuously perform self-cleaning and real-time measurement of the concentration of volatile gas molecules.

In accordance with an aspect of the present invention, a photo-ionization detector (PID) includes a microprocessor and a gas detection unit that measures a current corresponding to a concentration of a volatile gas in an ambient gas. The gas detection unit includes an ionization chamber, a UV lamp that ionizes the ambient gas in the ionization chamber, a bias electrode, and a measurement electrode. The microprocessor controls the gas detection unit such that the flow of the ambient gas in the ionization chamber is intermittently interrupted, and the UV lamp converts oxygen in the closed ambient gas to ozone.

The PID further includes a container that contains an oxygen-containing gas, which is supplied into the ionization chamber when the flow of the ambient gas is interrupted in the ionization chamber, so that the oxygen-containing gas is converted to ozone. The PID further includes a lamp driver, a bias driver circuit, and a measurement driver circuit. The microprocessor controls the lamp driver circuit, the bias driver circuit, and the measurement driver circuit.

The PID further includes a pump and a pump driver circuit, through which the microprocessor controls the pump. The pump is between the microprocessor and the gas detection unit, wherein the microprocessor intermittently closes the flow of the ambient gas in the ionization chamber by turning on and off the pump.

In accordance with another aspect of the present invention, a PID includes a microprocessor and multiple gas detection units. Each of the gas detection units measures a current corresponding to a concentration of a volatile gas in an ambient gas and includes an ionization chamber, a UV lamp, a bias electrode, and a measurement electrode. The microprocessor controls the gas detection units such that the flow of the ambient gas is prevented in the ionization chamber of at least one of the gas detection units while the ambient gas flow through the ionization chamber of at least another one of the gas detection units is permitted. The UV lamp converts oxygen in the closed ambient gas to ozone, which removes contamination in the ionization chamber with the closed ambient gas.

The PID further includes a container that contains an oxygen-containing gas, which is supplied into the ionization chamber, in which the flow of the ambient gas is prevented. The PID further includes a multi-port valve, a pump, and a pump driver circuit, through which the microprocessor controls the pump. The pump is between the microprocessor and the gas detection units, the pump moving the ambient gas through the ionization chambers of the gas detection units. The multi-port valve is coupled to the ionization chamber of each of the gas detection units and the pump, and opens and closes the ionization chamber of each of the plurality of the gas detection units to the flow of the ambient gas, while the pump is turned on.

In accordance with another aspect of the present invention, a PID includes a microprocessor, a first gas detection unit, and a second gas detection unit. The microprocessor controls the first and second gas detection units such that the ambient gas always flows through the ionization chamber of one of the gas detection units and the flow of the ambient gas is prevented in the ionization chamber of the other one of the gas detection units. The UV lamp converts oxygen in the closed ambient gas to ozone, which removes contamination in the ionization chamber with the closed ambient gas.

The PID further includes a container that contains an oxygen-containing gas, which is supplied into the ionization chamber, in which the flow of the ambient gas is prevented. The PID further includes a three-way valve, a pump, and a pump driver circuit, through which the microprocessor controls the pump. The pump is between the microprocessor and the gas detection units, the pump providing the ambient gas through the ionization chambers of the gas detection units. The three-way valve connected to the ionization chamber of each of the gas detection units and the pump permits ambient gas flow in the ionization chamber of one or the other of the gas detection units while the pump is turned on. The flow of ambient gas is permitted in the ionization chamber of one of the first and second gas detection units from which contamination has been removed during a time when ambient gas is prevented from flowing in the ionization chamber of the other of the first and second gas detection units to permit cleaning the ionization chamber of the other detection unit.

Another aspect of the present invention provides a method of real-time self-cleaning and measuring of a volatile gas concentration with a PID that comprises a gas detection unit including an ionization chamber, in which an ambient gas including a volatile gas is ionized by a UV lamp. The method includes causing the ambient gas to flow through the ionization chamber, to permit the PID to measure the volatile gas concentration, and causing the flow of the ambient gas through the ionization chamber and periodically interrupting the flow. The flow is on for a first period of time and off for a second period of time, and during the second period of time the UV lamp converts oxygen contained in the ambient gas to ozone to remove contamination in the ionization chamber. The method further includes supplying an oxygen-containing gas into the ionization chamber.

Flowing the ambient gas and stopping the flow of the ambient gas are repeated. The switch between flowing the ambient gas and stopping the flow of the ambient gas occurs by turning on and off a pump connected to the ionization chamber.

Still another aspect of the present invention provides a method of real-time self-cleaning and measuring of a volatile gas concentration with a PID that includes multiple gas detection units, each of the gas detection units including an ionization chamber, in which an ambient gas including a volatile gas is ionized by a UV lamp. The method includes flowing the ambient gas through the ionization chamber of one of the gas detection units, so that the PID measures the volatile gas concentration and stopping the flow of the ambient gas in the ionization chamber of another of the gas detection units so that the UV lamp converts oxygen contained in the ambient gas in the ionization chamber of the another gas detection unit to ozone, which removes contamination in the ionization chamber with the closed ambient gas.

The method further includes supplying an oxygen-containing gas into the ionization chamber in which the flow ambient gas is stopped.

Each of the gas detection units is repeatedly switched between flowing and stopping the ambient gas. The switch between flowing and stopping the ambient gas is achieved by using a multi-port valve connected between a pump and the ionization chamber of each of the gas detection units.

Still another aspect of the present invention provides a method of real-time self-cleaning and measuring of a volatile gas concentration with a photo-ionization detector (PID) that includes a first gas detection unit and a second gas detection unit, each of the gas detection units including an ionization chamber, in which an ambient gas including a volatile gas is ionized by a UV lamp. The method includes flowing the ambient gas through the ionization chamber of the first gas detection unit, so that the PID measures the volatile gas concentration, and stopping the ambient gas through the ionization chamber of the second gas detection unit so that the ambient gas is closed in the ionization chamber of the second gas detection unit while the ambient gas flows through the ionization chamber of the first gas detection unit. The UV lamp converts oxygen contained in the ambient gas in the ionization chamber of the second gas detection unit to ozone, which removes contamination in the ionization chamber of the second gas detection unit.

The method further includes supplying an oxygen-containing gas into the ionization chamber in which the flow of ambient gas is stopped.

Flowing and stopping the flow of ambient gas are repeatedly switched between the first and second gas detection units. The switch between flowing and stopping the flow of ambient gas is achieved by using a three-way valve connected between a pump and the ionization chamber of each of the gas detection units.

BRIEF DESCRIPTION OF DRAWINGS

Use of the same reference symbols in different drawings indicates similar or identical items.

DETAILED DESCRIPTION

The present invention is directed to photo-ionization detectors capable of self-cleaning and real-time measurement of the concentration of volatile gas molecules existing in the environment. The invention also provides methods that enable the photo-ionization detectors to continuously perform self-cleaning and real-time measurement of the concentration of volatile gas molecules.

Figure 1:
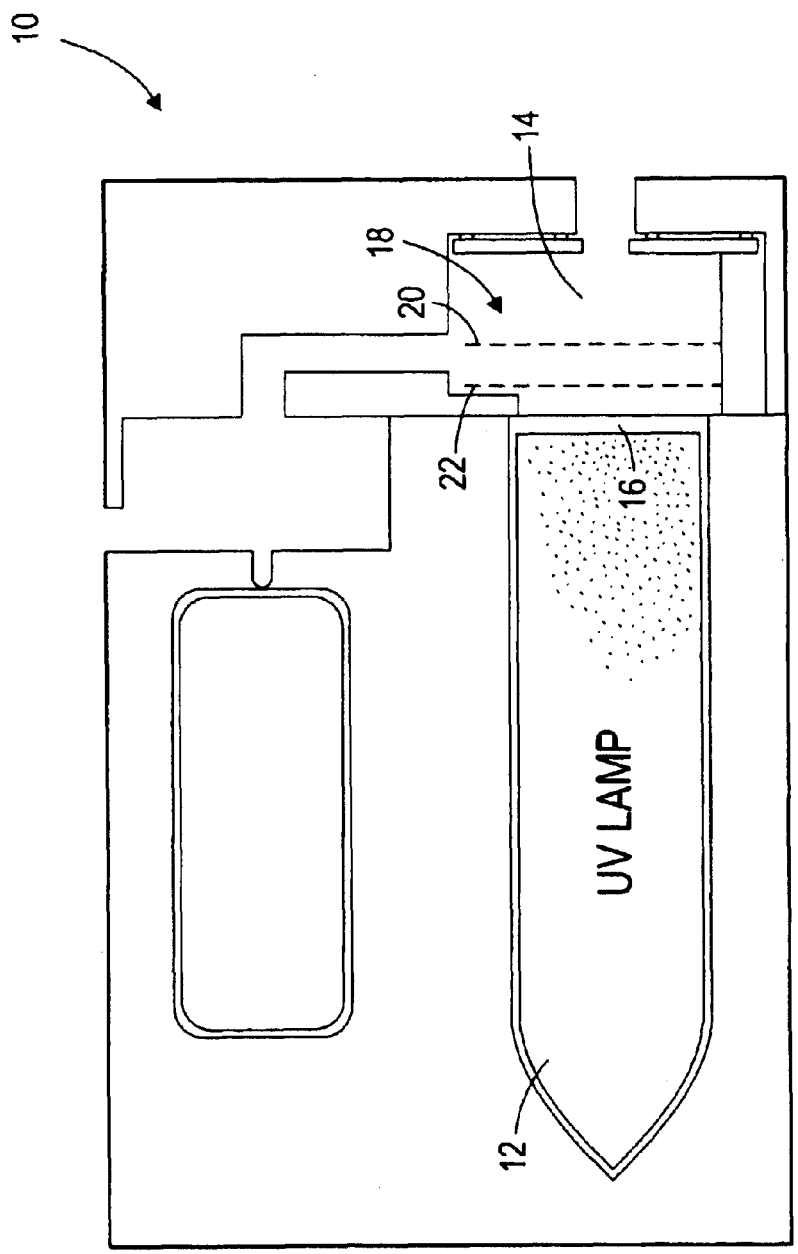
FIG. 1 is a block diagram of a conventional photo-ionization detector.
Figure 2:
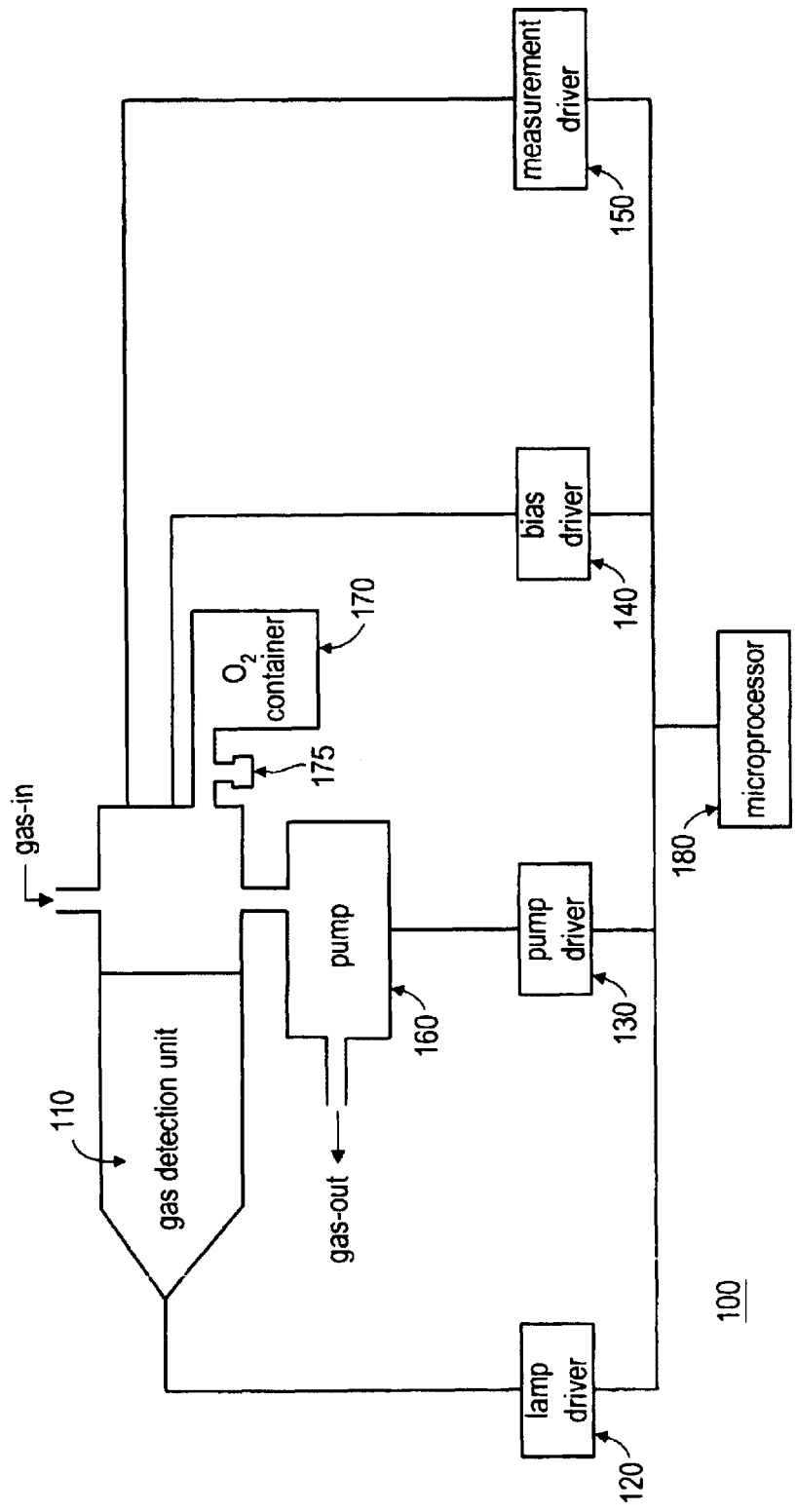
FIG. 2 is a block diagram of a photo-ionization detector in accordance with an embodiment of the present invention.
Figure 3:
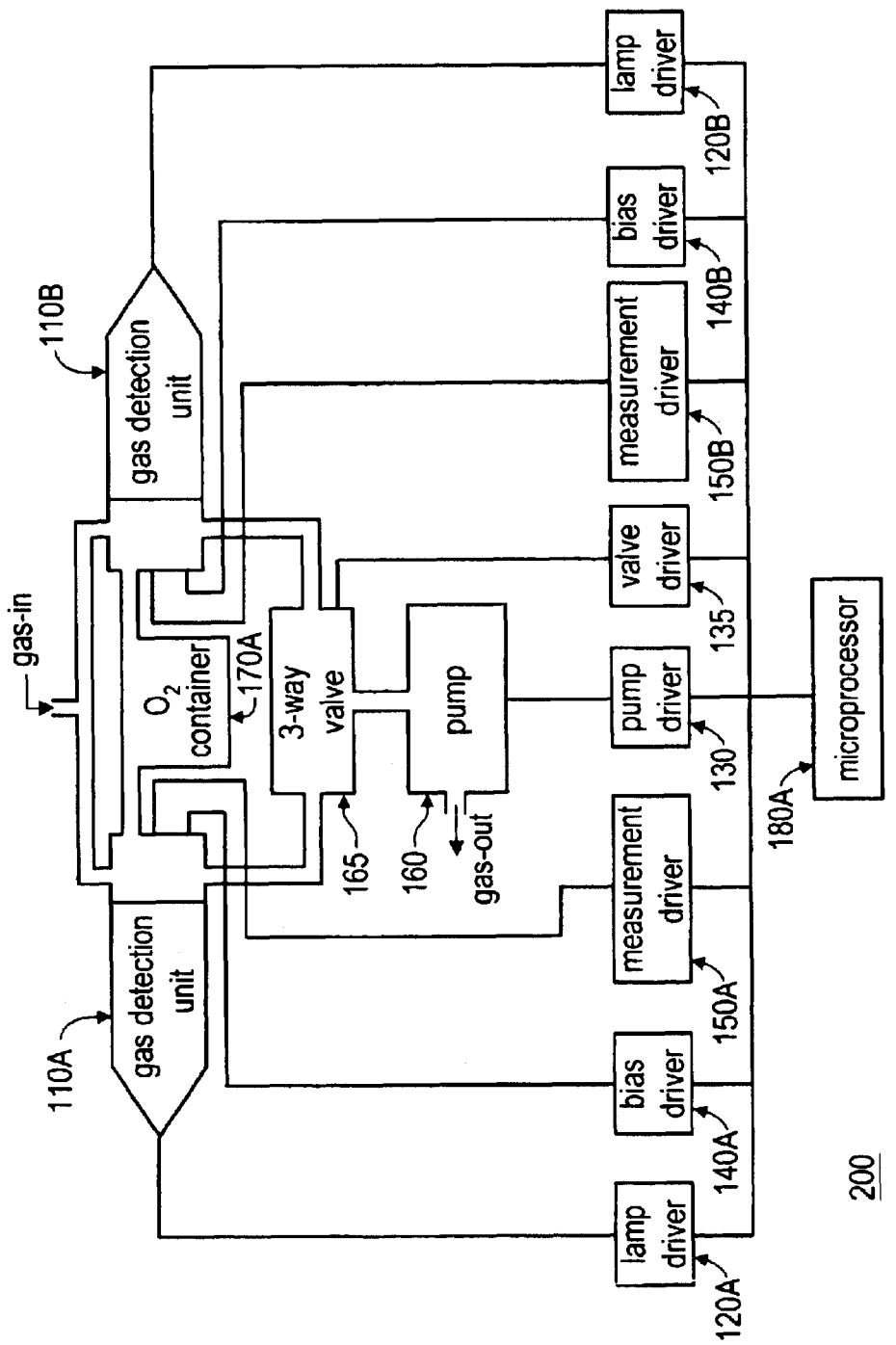
FIG. 3 is a block diagram of a photo-ionization detector in accordance with another embodiment of the present invention.
Figure 4:
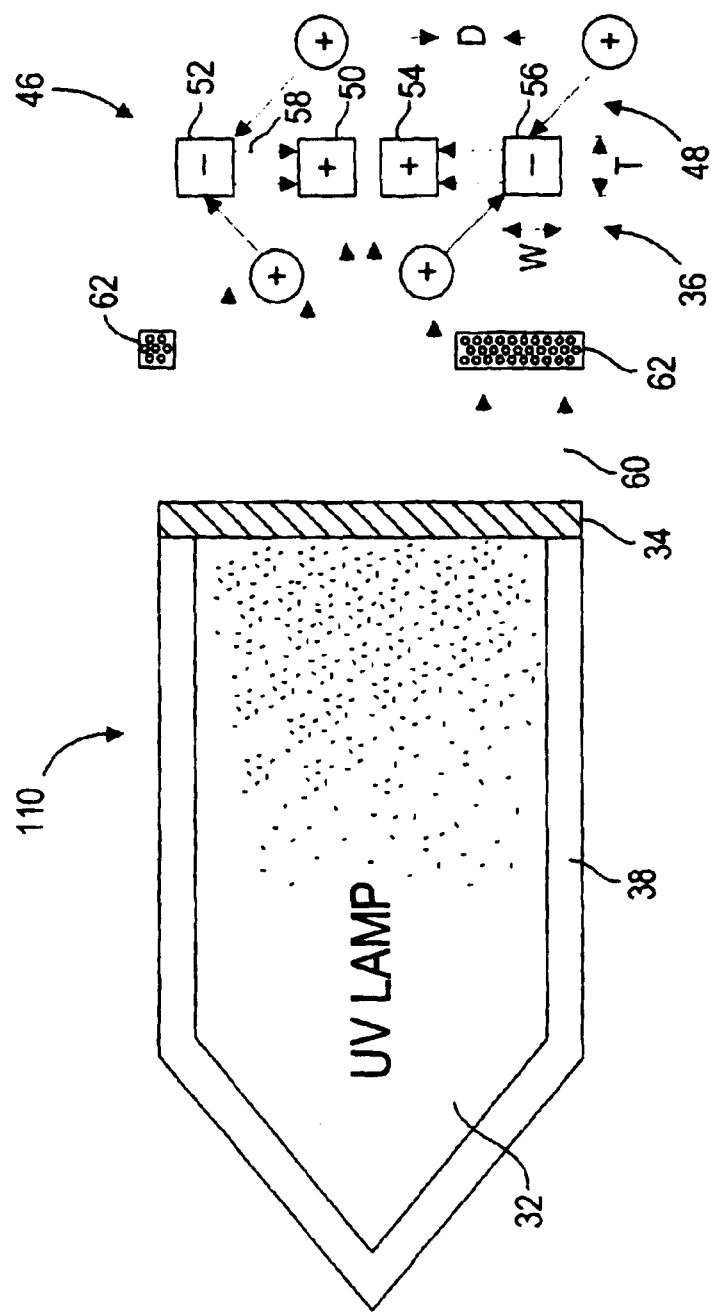
FIG. 4 is a cross-sectional view illustrating a volatile gas detection unit for the photo-ionization detectors of FIGS. 2 and 3.

FIG. 2 shows a photo-ionization detector (PID) 100 in accordance with an embodiment of the present invention, and FIG. 4 shows a volatile gas detection unit 110 for the PIDs 100 and 200 of FIGS. 2 and 3. PID 100 is a miniaturized and continuously opereated detector of volatile gases. PID 100 includes a volatile gas detection unit 110, an ultra-violet (UV) lamp driver circuit 120, a pump driver circuit 130, a bias driver circuit 140, a measurement driver circuit 150, a pump 160, an oxygen-containing gas container 170, and a microprocessor 180.

Referring FIGS. 2 and 4, gas detection unit 110 includes a UV lamp 32, which is sealed by an envelope 38, an optical window 34, and an ionization chamber 36. UV lamp 32 radiates UV photons or UV light 60 (e.g., light having a wavelength less than about 150 nm) through optical window 34 into ionization chamber 36. Envelope 38, which is preferably made of glass, contains a mixture of inert gases such as helium (e.g., 40%), argon (e.g., 30%) and krypton (e.g., 30%), at a reduced pressure (e.g., 25 Torr). Exemplary dimensions for envelope 38 are 0.10–1.00 inch in diameter and 0.20–2.00 inch in length. Optical window 34 is disposed at the end of envelope 38 and is made of a single crystal material. Depending on the material of choice for optical window 34, UV light having a desired energy level passes through optical window 34. For example, optical window 34 made of lithium fluoride (LiF), magnesium fluoride (MgF$_2$), barium fluoride (BaF$_2$), or calcium fluoride (CaF$_2$) allows the transmission of the UV light of 11.7 electron volts (eV), 10.6 eV, 9.8 eV, or 9.2 eV, respectively Gas detection unit 110 may be constructed as disclosed in a U.S. Pat. No. 6,313,638, entitled "DUAL-CHANNEL PHOTO-IONIZATION DETECTOR THAT ELIMINATES THE EFFECT OF ULTRAVIOLET INTENSITY ON CONCENTRATION MEASUREMENTS", issued Nov. 6, 2001. which is herein incorporated by reference in its entirety.

Lamp driver circuit 120 is connected to gas detection unit 110 to drive UV lamp 32. Microprocessor 180 can adjust the UV light intensity of UV lamp 32 by controlling lamp driver circuit 120. Details of the function and structure of lamp driver circuit 120 are described in the above-incorporated U.S. Pat. No. 6,225,633 and commonly owned U.S. Pat. No. 5,773,833 to Hsi, entitled "Photo-ionization Detector For Volatile Gas Measurement" and issued on Jun. 30, 1998, which is incorporated herein by reference in its entirety.

Referring to FIG. 4, the UV photons 60 from UV lamp 32 ionize volatile gas molecules inside ionization chamber 36. Ion detectors 46 and 48 disposed in ionization chamber 36 and positioned proximal to optical window 34 collect electrons and ions that result from the ionization of the volatile gas molecules. Each of ion detectors 46 and 48 includes a pair of electrodes, a bias electrode 50 or 54 and a measurement electrode 52 or 56. Bias electrodes 50 and 54 and measurement electrodes 52 and 56 are positioned in an interdigital arrangement. Each of bias and measurement electrodes 50, 54, 52, and 56 has at least a pair of digits, positioned in the interdigital arrangement. It is understood that bias and measurement electrodes 50, 54, 52, and 56 can each have from one to a number of digits. The above-incorporated U.S. Pat. No. 6,313,638 describes in detail the interdigital 10 arrangement, structures and fabrication methods of bias and measurement electrodes 50, 54, 52, and 56.

For instance, the digits of bias and measurement electrodes 50, 54, 52, and 56 can have straight or "step-like" shape and be formed by machine manufacturing various metals and alloys, preferably stainless steel. Bias and measurement electrodes 50, 54, 52, and 56 can also be formed by depositing a conductive electrode layer on a substrate, masking selected portions of the electrode layer, and etching and removing the remaining portions from the substrate to produce the interdigital electrode pattern. Subsequent to the etching process, the substrate is removed from the produced interdigital electrode. Alternatively, a transparent substrate may be used that allows UV light to be transmitted therethrough, thus avoiding the removal of the substrate. Alternatively, portions of the substrate can be removed to form a pattern that matches the interdigital electrode in shape. Examples of material used for the electrode layer and substrate include platinum on a ceramic substrate, copper on a printed circuit board, and gold on a silicon wafer.

The dimensions of bias and measurement electrodes 50, 54, 52, and 56 are about 0.01 to 0.20 inches in thickness T, most preferably about 0.02 inches, and about 0.01 to 0.08 inches in width W, most preferably about 0.02 inches. The distance or separation D between bias and measurement electrodes 50, 54, 52, and 56 is about 0.01 to 0.20 inches, most preferably about 0.03 inches. It is understood that these dimensions are illustrative in nature and that bias and measurement electrodes 50, 54, 52, and 56 can have other thickness, width, and separation.

Referring to FIGS. 2 and 4, gas detection unit 110 includes a UV shield 62 between optical window 34 and ion detectors 46 and 48 that shields measurement electrode 56 of ion detector 48 from UV light 60. During an operation of PID 100, UV light 60 striking ion detectors 46 and 48 can liberate electrons from electrodes 50, 52 and 54. Electrons liberated from bias electrodes 50 and 54 are, in general, attracted back to positive bias electrodes 50 and 54 and do not contribute to a base line current (i.e., a current presented even in the absence of ionizable gases) in respective ion detectors 46 and 48. However, bias electrodes 50 and 54 can capture electrons liberated from measurement electrodes 52 and 56 which leads to a base line current. UV shield 62, which is preferably made of a polytetrafluoroethene (Teflon) sheet, is between optical window 34 and measurement electrode 56 and stops UV light 60 from striking measurement electrode 56. Even though, as shown in FIG. 2, this embodiment completely shields measurement electrode 56 from UV light 60 and completely exposes measurement electrode 52, another embodiment allows UV light 60 to strike electrodes 52 and 56 at different degrees. In other words, UV shield 62 differentially exposes electrodes 52 and 56 to UV light 60. Alternatively, a layer of material (not shown) which is inert to the gases and ions generated in ionization chamber 36, has an electrical insulation property, and is opaque to high energy UV light may be employed as a UV shield on electrode 56. For example, a photo-resist polymer made of polytetrafluoroethene (Teflon) or a ceramic layer made of alumina may be formed on a surface of measurement electrode 56 facing optical window 34 to serve as a UV shield. The UV shield as just described may also be employed for bias electrodes 50 and 54.

In collecting the electrons and the ions, measurement electrodes 52 and 56 are near ground voltage and separated from bias electrodes 50 and 54 to create an electrical field 58. For instance, bias driver circuit 140 provides a positive bias voltage (e.g., DC voltage of about 4–120V) to bias electrodes 50 and 54. Measurement driver circuit 150 is connected to measurement electrodes 52 and 56 and measures the electrical currents caused by the collection of the ions, i.e., the measurement currents. The above-incorporated U.S. Pat. No. 5,773,833 patent discloses embodiments of measurement driver circuit 150. Microprocessor 180 communicates with both bias driver circuit 140 and measurement driver circuit 150 and can adjust the bias voltage that bias driver circuit 140 applies to bias electrodes 50 and 54. Measurement driver circuit 150 sends signals indicative of the measurement currents measured at detectors 46 and 48 to microprocessor 180 in order to determine the concentration of the volatile gas molecules. Based on pre-calibration data, microprocessor 180 converts the current signal into an equivalent concentration of gases. Details of the determination of the volatile gas concentration is are disclosed in the above-incorporated U.S. Pat. No. 6,313,638.

After extended use of PID 100, the UV intensity in gas detection unit 110 can vary for a variety of reasons, including degradation of the electrical performance of UV lamp 32, contamination of optical window 34 by polymer-like substances, and presence of interfering substances (i.e., substances which can absorb or enhance UV photons, e.g., methane, water, carbon monoxide, nitrogen, etc.).

Referring to FIGS. 2 and 4, PID 100 includes pump 160 and pump driver circuit 130 to control the flow of gases into and out of ionization chamber 36 of gas detection unit 110. Pump 160 is connected to pump driver circuit 130, which in turn is connected to microprocessor 180 for controlling pump 160.

Ionization chamber 36 is an open volume chamber, receiving a laminar flow of gases. Pump 160 provides a flow of gases (e.g., 200–600 ml/min) into and out of ionization chamber 36. When pump 160 is turned off, gases are prevented from flowing into or out of ionization chamber 36. The laminar flow of gases through ionization chamber 36 is parallel to a plane defined by the surface of optical window 34. Furthermore, the flow of gases is perpendicular to electrical field 58 of bias and measurement electrodes 50, 54, 52, and 56. Thus, gases flow easily between bias and measurement electrodes 50, 54, 52, and 56, and more ions are collected by measurement electrodes 52 and 56. The flow of gases is also perpendicular to the direction of propagation of UV light 60. Accordingly, the perpendicular relationship between UV light 60 and the gas flow facilitates ionization of a greater percentage of gas molecules between electrodes 50 and 52 and 54 and 56, and also allows for a greater collection of the ion molecules by measurement electrodes 52 and 56.

As described above, extended use of PID 100 can build up contamination in ionization chamber 36, including on bias and measurement electrodes 50, 54, 52, and 56 and optical window 34, and thus diminish effectiveness of PID 100. Typically, the contamination includes a coating of metal atoms, oil film, dust particles, and other polymer-like coating substances. Accordingly, the contamination must be removed regularly.

PID 100 includes oxygen-containing gas container 170 and an oxygen pump 175 for real-time self-cleaning of ionization chamber 36. In operating PID 100, microprocessor 180 turns pump 160 on and off while maintaining transmission of UV lamp 32 for self-cleaning. When microprocessor 180 turns pump 160 on, ambient gases flow through ionization chamber 36, so that the volatile gas concentration in the ambient gases is measured. While pump 160 is turned on, microprocessor 180 turns off the oxygen pump such that an oxygen-containing gas in container 170 is not introduced into ionization chamber 36.

For real-time self-cleaning of PID 100, microprocessor 180 turns off pump 160 intermittently. When pump 160 is turned off, the ambient gases are prevented from entering into and exiting out of ionization chamber 36, and microprocessor 180 turns on the oxygen pump to supply the oxygen-containing gas into ionization chamber 36. Then, UV light 60 converts oxygen, enclosed in ionization chamber 36, to ozone. Ozone, a strong oxidant, accumulates in ionization chamber 36 and oxidizes, i.e., etches and removes, contamination from ionization chamber 36, including surfaces of bias and measurement electrodes 50, 54, 52, and 56 and optical window 34. After the contamination has been etched and removed, pump 160 is turned on again to flush and discharge the contamination out of ionization chamber 36 and to introduce the ambient gases into ionization chamber 36 to continue to measure the volatile gas concentration of the ambient gases.

In summary, for real-time self-cleaning, microprocessor 180 repeatedly turns pump 160 and oxygen pump 190 on and off. In some environments, if pump 160 is turned on and off sufficiently frequently, i.e., every 0.5 second, PID 100 can measure the volatile gas concentration every second and continuously clean ionization chamber 36. Depending on the size of chamber, the rate at which contamination builds up, the flow rate of the sampling pump, and the amount of oxygen and volatile gas compound in the gas sample, self-cleaning may require several minutes. In addition, when the ambient gas includes such an amount of oxygen that it can produce enough ozone to remove the contamination in ionization chamber 36, the introduction of the oxygen-containing gas into ionization chamber 36 is not necessary.

In addition to controlling lamp driver circuit 120, pump driver circuit 130, bias driver circuit 140, and measurement circuit 150, microprocessor 180 may also execute firmware. The firmware provides a user interface for controlling PID 100, displaying the volatile gas concentration, and generating warning signals if the volatile gas concentration reaches designated threshold levels. Controls, an alarm, and a liquid crystal display (not shown) provide a hardware portion of the user interface. A non-volatile memory such as a ROM, EEROM, or Flash Memory (not shown) contains the firmware and parameters for calibration of PID 100. A volatile memory may also be required unless microprocessor 180 contains sufficient on-chip memory for execution of the firmware.

FIG. 3 illustrates a PID 200 in accordance with another embodiment of the present invention. PID 200 includes two gas detection units 110A and 110B, two lamp driver circuits 120A and 120B, a pump driver circuit 130, two bias driver circuits 140A and 140B, two measurement driver circuits 150A and 150B, a valve driver circuit 135, a pump 160, a three-way valve 165, and a microprocessor 180A.

Gas detection units 110A and 110B, lamp driver circuits 120A and 120B, pump driver circuit 130, bias driver circuits 140A and 140B, and measurement driver circuits 150A and 150B, pump 160 may be implemented identically to gas detection unit 110, lamp driver circuit 120, pump driver circuit 130, bias driver circuit 140, measurement driver circuit 150, and pump 160 of FIG. 2, respectively. Microprocessor 180A of PID 200 is of course programmed differently from microprocessor 180 of PID 100 since microprocessor 180A provides additional controls as described below. Lamp driver circuit 120A, bias driver circuit 140A, and measurement driver circuit 150A are for operating gas detection unit 110A, and lamp driver circuit 120B, bias driver circuit 140B, and measurement driver circuit 150B are for operating gas detection unit 110B. As in PID 100 of FIG. 2, microprocessor 180A of PID 200 operates gas detection units 110A and 110B by controlling lamp driver circuits 120A and 120B, pump driver circuit 130, bias driver circuits 140A and 140B, and measurement driver circuits 150A and 150B.

Three-way valve 165 is connected to each of gas detection units 110A and 110B and pump 160, and valve driver circuit 135 is connected between microprocessor 180 and three-way valve 165. Microprocessor 180A controls valve driver circuit 135 such that, when pump 160 is on, a flow of ambient gas occurs either through the ionization chamber of gas detection unit 110A or through the ionization chamber of gas detection unit 110B.

Referring to FIG. 3, pump 160 is always on during the operation of PID 200, while pump 160 is intermittently on and off during the operation of PID 100. For accomplishing real-time self-cleaning, instead of the repeated turn-on-and-off, one of gas detection units 110A and 110B is employed to measure the volatile gas concentration, while the other is in a self-cleaning cycle. After the self-cleaning cycle is finished, the self-cleaned gas detection unit 110A or 110B measures the volatile gas concentration, and the other one 110A or 110B is self-cleaned. Like PID 100, PID 200 always turns on the UV lamps of gas detection units 110A and 110B.

During the continuous operation of PID 200, the interchange between gas detection units 110A and 110B for self-cleaning and measurement is accomplished by three-way valve 165. Microprocessor 180A intermittently switches the opening of inlets (not shown) of three-way valve 165, which are connected to the outlets of the ionization chambers of gas detection units 110A and 110B, respectively. When the inlet of three-way valve 165 connected to gas detection unit 110A is opened, the inlet of three-way valve 165 connected to the outlet of gas detection unit 110B is closed. Then, pump 160 produces a flow of ambient gas through the ionization chamber of gas detection unit 110A, so that gas detection unit 110A sends a current signal corresponding to the volatile gas concentration of the ambient gas to microprocessor 180A. While gas detection unit 110A is measuring the volatile gas concentration, gas detection unit 110B self-cleans by converting the oxygen contained in the ambient gas closed in the ionization chamber of gas detection unit 110B as described with respect of PID 100 of FIG. 2.

After a predetermined period of time, e.g. a few minutes, microprocessor 180A switches the opening of the inlets of three-way valve 165, such that the inlet of three-way valve 165 to gas detection unit 110A is closed and the inlet of three-way valve 165 connected to gas detection unit 110B is opened. Then, gas detection unit 110A self-cleans, and gas detection unit 110B measures the volatile gas concentration. PID 200 repeats such a switching procedure of measuring and self-cleaning to keep both gas detection units 110A and 110B clean and measure the volatile gas concentration without interruption.

Although PID 200 employs only two gas detection units, another PID according to the present invention may integrate three or more gas detection units for real-time self cleaning and uninterrupted measuring of the volatile gas concentration. When three or more gas detection units are used, a multi-port valve is used instead of three-way valve 165 of FIG. 3. In addition, where the ambient gas includes oxygen insufficient to provide the cleaning required, an oxygen-containing gas can be provided into PID 200 in a similar way that was described with respect to PID 100. An oxygen-containing gas container 170A and an oxygen pump (not shown) of PID 200 are connected to the ionization chambers of gas detection units 110A and 110B, so that the oxygen-containing gas is supplied into the ionization chamber of gas detection unit 110A or 110B, in which the flow of the ambient gas was stopped.

Although the invention has been described with reference to particular embodiments, the description is only an example of the inventors' application and should not be taken as limiting. Various adaptations and combinations of features of the embodiments disclosed are within the scope of the invention as defined by the following claims.

What is claimed is:

1. A photo-ionization detector (PID) comprising:
   a control unit; and
   a gas detection unit that measures a current corresponding to a concentration of a volatile gas in an ambient gas, wherein the gas detection unit comprises:
   an ionization chamber, through which the ambient gas flows;
   a UV lamp that ionizes the ambient gas in the ionization chamber;
   a bias electrode that is biased to repel positive ions resulting from the ionization of the ambient gas; and
   a measurement electrode that is biased to attract positive ions resulting from the ionization of the ambient gas,
   wherein the control unit controls the gas detection unit such that a flow of the ambient gas in the ionization chamber is intermittently interrupted, wherein the UV lamp converts oxygen in the closed ambient gas to ozone.

2. The PID of claim 1, further comprising a container coupled to the ionization chamber, the container including an oxygen-containing gas, wherein the oxygen-containing gas is supplied into the ionization chamber when the flow of the ambient gas is interrupted in the ionization chamber, so that the oxygen-containing gas is converted to ozone.

3. The PID of claim 1, further comprising a pump coupled to the ionization chamber, wherein the control unit intermittently closes the flow of the ambient gas in the ionization chamber by turning on and off the pump.

4. The PID of claim 3, further comprising a pump driver circuit coupled to the pump, wherein the control unit controls the pump driver circuit.

5. The PID of claim 3, wherein the pump is turned on and off every 0.5 second.

6. The PID of claim 1, further comprising:
   a lamp driver circuit that drives the UV lamp;
   a bias driver circuit that provides a first voltage to the bias electrode; and
   a measurement driver circuit that provides a second voltage to the measurement electrode,
   wherein the control unit controls the lamp driver circuit, the bias driver circuit, and the measurement driver circuit.

7. A photo-ionization detector (PID) comprising:
   a control unit;
   a UV lamp: and
   a plurality of gas detection units, each of the plurality of gas detection units measuring a current corresponding to a concentration of a volatile gas in an ambient gas, wherein each of the plurality of the gas detection units comprises:
   an ionization chamber, through which the ambient gas flows;
   a bias electrode that is biased to attract positive ions resulting from the ionization of the ambient gas; and a measurement electrode that is biased to attract positive ions resulting from the ionization of the ambient gas, wherein the control unit controls the plurality of gas detection units such that a flow of the ambient gas is prevented in the ionization chamber of at least one of the plurality of gas detection units while the ambient gas flow through the ionization chamber of at least another one of the plurality of gas detection units is permitted, wherein the UV lamp converts oxygen in the closed ambient gas to ozone.

8. The PID of claim 7, further comprising a container coupled to the ionization chamber, the container including an oxygen-containing gas, wherein the oxygen-containing gas is supplied to the ionization chamber in which a flow of the ambient gas is prevented, so that the oxygen-containing gas is converted to ozone.

9. The PID of claim 7, further comprising a pump coupled to each of the plurality of gas detection units, the pump moving the ambient gas through the ionization chamber of the plurality of gas detection units.

10. The PID of claim 9, further comprising a pump driver circuit coupled to the pump, wherein the control unit controls the pump driver circuit.

11. The PID of claim 9, further comprising a multi-port valve coupled to the ionization chamber of each of the plurality of gas detection units, wherein the multi-port valve opens and closes the ionization chamber of each of the plurality of the gas detection units to the flow of the ambient gas.

12. The PID of claim 11, further comprising a valve driver circuit coupled to the multi-port valve, wherein the control unit controls the multi-port valve driver circuit.

13. The PID of claim 11, wherein the pump operates continuously.

14. The PID of claim 7, wherein the flow of ambient gas is permitted in the ionization chamber of one of the gas detection units from which contamination has been removed during a time when ambient gas is prevented from flowing in the ionization chamber of another of the gas detection units to permit cleaning the ionization chamber of the another.

15. The PID of claim 7, wherein each of the gas detection units has associated therewith a lamp driver circuit that drives the UV lamp of the gas detection unit;

a bias driver circuit that provides a first voltage to the bias electrode of the gas detection unit; and a measurement driver circuit that provides a second voltage to the measurement electrode of the gas detection unit, wherein the control unit controls the lamp driver circuits, the bias driver circuits, and the measurement driver circuits.

16. A photo-ionization detector (PID) comprising:

a microprocessor;

a first gas detection unit; and a second gas detection unit, each of the first and second gas detection units measuring a current corresponding to a concentration of a volatile gas in an ambient gas, wherein each of the first and second the gas detection units comprises:

an ionization chamber, through which the ambient gas flows;

a UV lamp that ionizes the ambient gas in the ionization chamber;

a bias electrode that is biased to repel positive ions resulting from the ionization of the ambient gas; and a measurement electrode that is biased to attract positive ions resulting from the ionization of the ambient gas, wherein the microprocessor controls the first and second gas detection units such that the ambient gas flows through the ionization chamber of one of the first and second gas detection units and the flow of the ambient gas is prevented in the ionization chamber of the other of the first and second gas detection units, wherein the UV lamp converts oxygen in the other of the first and second gas detection units to ozone.

17. The PID of claim 16, further comprising a container coupled to the ionization chamber of the first and second gas detection units, the container including an oxygen-containing gas, wherein the oxygen-containing gas supplied to the ionization chamber in which ambient flow is prevented, so that the oxygen-containing gas is converted to ozone.

18. The PID of claim 16, further comprising a pump coupled to the first and second gas detection units, the pump providing the ambient gas flow through the ionization chambers of the gas detection units.

19. The PID of claim 18, further comprising a pump driver circuit coupled to the pump, wherein the microprocessor controls the pump driver circuit.

20. The PID of claim 16, further comprising a three-way valve coupled to the ionization chamber of each of the first and second gas detection units, wherein the three-way valve permits ambient gas flow in the ionization chamber of one or the other of the first and second gas detection units.

21. The PID of claim 20, further comprising a valve driver circuit coupled to the three-way valve, wherein the microprocessor controls the valve driver circuit to control the three-way valve.

22. The PID of claim 20, wherein the pump is connected to the three-way valve and operates continuously.

23. The PID of claim 16, wherein the flow of ambient gas is permitted in the ionization chamber of one of the first and second gas detection units from which contamination has been removed during a time when ambient gas is prevented from flowing in the ionization chamber of the other of the first and second gas detection units to permit cleaning the ionization chamber of the other.

24. The PID of claim 16, wherein each of the first and second gas detection units has associated therewith a lamp driver circuit that drives the UV lamp of the gas detection unit;

a bias driver circuit that provides a first voltage to the bias electrode of the gas detection unit; and a measurement driver circuit that provides a second voltage to the measurement electrode of the gas detection unit, wherein the microprocessor controls the lamp driver circuits, the bias driver circuits, and the measurement driver circuits.

25. A method of real-time self-cleaning and measuring of a volatile gas concentration with a photo-ionization detector (PID) that comprises a gas detection unit including an ionization chamber in which an ambient gas including a volatile gas is ionized by a UV lamp, the method comprising:

causing ambient gas to flow through the ionization chamber, to permit the PID to measure the volatile gas concentration; and causing the flow of the ambient gas through the ionization chamber and periodically interrupting the flow, wherein the flow is on for a first period of time and off for a second period of time, and further wherein during the second period of time the UV lamp converts oxygen contained in the ambient gas to ozone to remove contamination in the ionization chamber.

26. The method of claim 25, further comprising supplying an oxygen-containing gas into the ionization chamber.

27. The method of claim 25, wherein the first and second periods of time are each one-half second.

28. The method of claim 25, wherein the interruption of the flow of the ambient gas is achieved by turning on and off a pump connected to the ionization chamber.

29. A method of real-time self-cleaning and measuring of a volatile gas concentration with a photo-ionization detector (PID) that comprises a plurality of gas detection units, each of the plurality of gas detection units including an ionization chamber, in which an ambient gas including a volatile gas is ionized by a UV lamp, the method comprising:

flowing the ambient gas through the ionization chamber of one of the plurality of gas detection units so that the PID measures the volatile gas concentration; and stopping the flow of the ambient gas in the ionization chamber of another of the plurality of gas detection units so that the UV lamp converts oxygen contained in the the ionization chamber of the another gas detection unit to ozone, which removes contamination in the ionization chamber with the closed ambient gas, wherein each of the plurality of gas detection units is repeatedly switched between flowing and stopping the ambient gas.

30. The method of claim 29, further comprising supplying an oxygen-containing gas into the ionization chamber in which the flow of ambient gas is stopped.

31. The method of claim 29, wherein the switch between the flowing and stopping of the flow of ambient gas is achieved by using a multi-port valve connected between a pump and the ionization chamber of each of the plurality of gas detection units.

32. A method of real-time self-cleaning and measuring of a volatile gas concentration with a photo-ionization detector (PID) that comprises a first gas detection unit and a second gas detection unit, each of the first and second gas detection units including an ionization chamber, in which an ambient gas including a volatile gas is ionized by a UV lamp, the method comprising:

flowing the ambient gas through the ionization chamber of the first gas detection unit, so that the RID measures the volatile gas concentration; and stopping the ambient gas through the ionization chamber of the second gas detection unit so that the ambient gas is closed in the ionization chamber of the second gas detection unit while the ambient gas flows through the ionization chamber of the first gas detection unit, wherein the UV lamp converts oxygen contained in the ambient gas in the ionization chamber of the second gas detection unit to ozone, which removes contamination in the ionization chamber of the second gas detection unit, wherein the flowing and stopping the ambient gas are repeatedly switched between the first and second gas detection units.

33. The method of claim 32, further comprising supplying an oxygen-containing gas into the ionization chamber in which the flow of ambient gas is stopped.

34. The method of claim 32, wherein the switch between the flowing and stopping of the flow of ambient gas is achieved by using a three-way valve connected between a pump and the ionization chamber of each of the first and second gas detection units.

* * * * *